US 8,084,024 B2

(12) United States Patent
Mackay

(10) Patent No.: US 8,084,024 B2
(45) Date of Patent: Dec. 27, 2011

(54) METHOD FOR PRODUCING ANTIBODIES

(75) Inventor: Charles Reay Mackay, Vaucluse (AU)

(73) Assignee: G2 Inflammation Pty Ltd (AU)

( * ) Notice: Subject to any disclaimer, the term of this patent is extended or adjusted under 35 U.S.C. 154(b) by 75 days.

(21) Appl. No.: 12/375,845

(22) PCT Filed: Aug. 22, 2007

(86) PCT No.: PCT/AU2007/001208
§ 371 (c)(1),
(2), (4) Date: Jan. 30, 2009

(87) PCT Pub. No.: WO2008/022391
PCT Pub. Date: Feb. 28, 2008

(65) Prior Publication Data
US 2009/0312526 A1    Dec. 17, 2009

Related U.S. Application Data

(60) Provisional application No. 60/839,550, filed on Aug. 22, 2006.

(51) Int. Cl.
*A01N 63/00* (2006.01)
*A61K 39/395* (2006.01)
*A01K 67/00* (2006.01)

(52) U.S. Cl. ............... 424/93.2; 424/809; 800/8

(58) Field of Classification Search .............. None
See application file for complete search history.

(56) References Cited

U.S. PATENT DOCUMENTS 5,480,974 A * 1/1996 Morgan et al. ............ 530/387.9

FOREIGN PATENT DOCUMENTS

| WO | WO-9401547 A2 | 1/1994 |
| WO | WO-2005060739 A1 | 7/2005 |

OTHER PUBLICATIONS

Extended European Search Report for European Patent Application No. 07784845.5 mailed May 12, 2010. 7 pages.
Pacasova R. et al. "Cell Surface Detection of HLA-E Gene Products with a Specific Monoctonal Antibody." *Journal of Reproductive Immunology*. Jul. 1999. vol. 43, No. 2. pp. 195-201. XP002579832ISSN: 0165-0378.
Sireci G. et al. "Analysis of the Immune Response Induced by a Single Xenoantigen in Vivo." *Immunology Letters*. Elsevier BV, Netherlands. vol. 98, No. 2. May 15, 2005. pp. 245-252. XP004862746ISSN: 0165-2478.
Watanabe, H. et al. "Analysis of C5a Receptor by Monoclonal Antibody." *Journal of immunological Methods*. Elsevier Science Publishers B.V., Amsterdam, Netherlands. vol. 185, No. 1. Sep. 11, 1995. pp. 19-29. XP0040211511ISSN: 0022-1759.
Disanto, J. et al. "Generation of anti-human CD8β-specific antibodies using transfectants expressing mixed-species CD8 heterodimers." Journal of Immunological Methods. 1991. vol. 141. pp. 123-131.
International Search Report and Written Opinion for International Patent Application No. PCT/AU2007/001208 mailed Oct. 26, 2007 (4 pages).
Lee, H. et al. Human C5aR knock-in mice facilitate the production and assessment of anti-inflammatory monoclonal antibodies. Nature Biotechnology. Oct. 2006. vol. 24, No. 10. pp. 1279-1284. Sep. 17, 2006.

* cited by examiner

*Primary Examiner* — Michail Belyavskyi
(74) *Attorney, Agent, or Firm* — K&L Gates LLP; Ann-Louise Kerner

(57) ABSTRACT

The present invention relates to a method for producing antibodies and to antibodies produced by this method. In one embodiment the invention relates to a method for producing an antibody that binds to a polypeptide of a first species, the method comprising immunizing a mammal of a second species with cells derived from a transgenic mammal of the second species, wherein the polypeptide of the first species is expressed on the surface of the cells derived from the transgenic mammal.

11 Claims, 9 Drawing Sheets

METHOD FOR PRODUCING ANTIBODIES

CROSS REFERENCE TO RELATED APPLICATIONS

This application is a national stage application under 35 U.S.C. §371 of International Patent Appln. PCT/AU2007/001208, designating the United States and filed on Aug. 22, 2007, which claims the benefit of priority under 35 U.S.C. §119(a) to U.S. Appln. No. 60/839,550, filed Aug. 22, 2006, each of which is incorporated herein by reference.

FIELD OF THE INVENTION

The present invention relates to a method for producing antibodies and to antibodies produced by this method.

BACKGROUND OF THE INVENTION

Antibodies represent a class of therapeutic molecules with applications in many different areas including transplantation, cardiovascular diseases, infectious diseases, cancer, and autoimmunity. The development of hybridoma technology has enabled the isolation of monoclonal antibodies (also referred to as MAbs) as candidate therapeutic molecules. MAbs now constitute a rapidly growing class of therapeutic, due in part to their predictable pharmacokinetic properties, their high success rate in the clinic, and their ability to antagonize large protein-protein interactions.

Chemoattractant receptors represent a class of G-protein coupled receptors that facilitate cell migration (Gerard, et al., *Ann. Rev. Immunol.* 12:775-808 (1994a); Gerard, et al., *Curr. Opin. Immunol.* 6:140-145 (1994b); Murphy, *Ann. Rev. Immunol.* 12:593-633 (1994)). These receptors have attracted the interest of numerous pharmaceutical companies, since they are usually amenable to inhibition by organic small molecules, and blocking these receptors or their ligands ameliorates various inflammatory conditions, at least in animal models (Mackay, *Nat. Immunol.* 2:95-101 (2001); von Andrian, et al., *N. Engl. J. Med.* 343:1020-1034 (2000); and Luster, et al., *Nat. Immunol.* 6:1182-1190 (2005)). One receptor that plays a critical role in numerous inflammatory conditions is the receptor for C5a (C5aR) (Gerard, et al., *Curr. Opin. Immunol.* 6:140-145 (1994b); Guo, et al., *Ann. Rev. Immunol.* 23:821-852 (2005); Riedemann, et al., *J. Clin. Invest.* 112:460-467 (2003); Ji, H., et al., *Immunity* 16:157-168 (2002)). Considerable effort has gone to developing human C5aR antagonists, including organic small molecules and peptide antagonists (Sumichika, *Curr. Opin. Investig. Drugs* 5:505-510 (2004); Allegretti, et al., *Curr. Med. Chem.* 12:217-236 (2005)). Despite this effort, the development of suitable small molecule antagonists for C5aR and other chemoattractant receptors has proven problematic.

Recently, monoclonal antibodies (mAbs) have proven to be useful agents to antagonize chemoattractant receptors, and to identify important regions for chemokine/ligand binding, or HIV-I binding (Heath, et al., *J. Clin. Invest.* 99:178-184 (1997)). However, the generation of high affinity antagonistic mAbs to chemoattractant receptors has also proven difficult in the past. There is therefore a need for an improved method for generating high affinity antibodies against polypeptides such as G-protein coupled receptors and chemoattractant receptors.

SUMMARY OF THE INVENTION

The present inventors have now found that that transgenic mice expressing a human polypeptide can be used to develop high affinity antagonistic mAbs against the human polypeptide, through immunization of wild-type mice with cells derived from the transgenic mice.

Accordingly, the present invention provides a method for producing an antibody against a polypeptide of a first species, the method comprising: immunizing a mammal of a second species with cells derived from a transgenic mammal of the second species, wherein the polypeptide of the first species is expressed by the cells derived from the transgenic mammal.

In a preferred embodiment, the polypeptide of the first species is expressed on the surface of the cells derived from the transgenic mammal.

In a further preferred embodiment, the method includes the additional step of preparing hybridoma cells from cells, preferably spleen cells, obtained from the immunized mammal. Preferably, the method further comprises screening the hybridoma cells for antibodies that bind to the polypeptide of the first species.

In a preferred embodiment of the present invention, the antibody is a MAb. The invention also encompasses recombinant or humanized antibodies that are derived from antibodies produced by the present invention.

In a preferred embodiment of the present invention, the first species is a domestic animal, a livestock animal or a human. More preferably, the first species is a human.

In a further preferred embodiment, the second species is selected from the group consisting of cow, pig, goat, sheep, camel, horse, cat, dog, monkey, baboon, rabbit, guinea pig, rat, hamster and mouse. Rodents such as rats, mice and hamsters are preferred mammals of the second species. More preferably, the second species is a mouse.

It will be appreciated that the polypeptide of the first species may be any therapeutic or diagnostic target of interest. For example, the polypeptide may be a G-protein coupled receptor. In a preferred embodiment, the G-protein coupled receptor is a chemoattractant receptor. Preferably the chemoattractant receptor is C5aR.

In another embodiment the nucleic acid molecule encoding the polypeptide has been genetically modified in order to enhance expression of the polypeptide in the cells of the transgenic mammal.

In a further preferred embodiment the cells derived from the transgenic mammal are cells that express high levels of the polypeptide of the first species. The preferred cell type will therefore depend on the nature of the polypeptide. For example, if the polypeptide is naturally highly expressed in the liver, the preferred cells derived from the transgenic mammal may be liver cells. Alternatively, if the polypeptide affects immune regulation or inflammatory responses, the preferred cell type may be cells of the immune system, such as antigen presenting cells. Examples of suitable antigen presenting cells include dendritic cells, macrophages, monocytes, neutrophils, eosinophils, basophils, fibroblasts, mast cells, T cells and B cells.

In yet a further preferred embodiment, the cells derived from the transgenic mammal are cells that have been genetically modified so as to express high levels of the polypeptide of the first species.

The present invention also provides an antibody produced by the method of the present invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The following figures are presented for the purpose of illustration only, and are not intended to be limiting.

Figure 1:
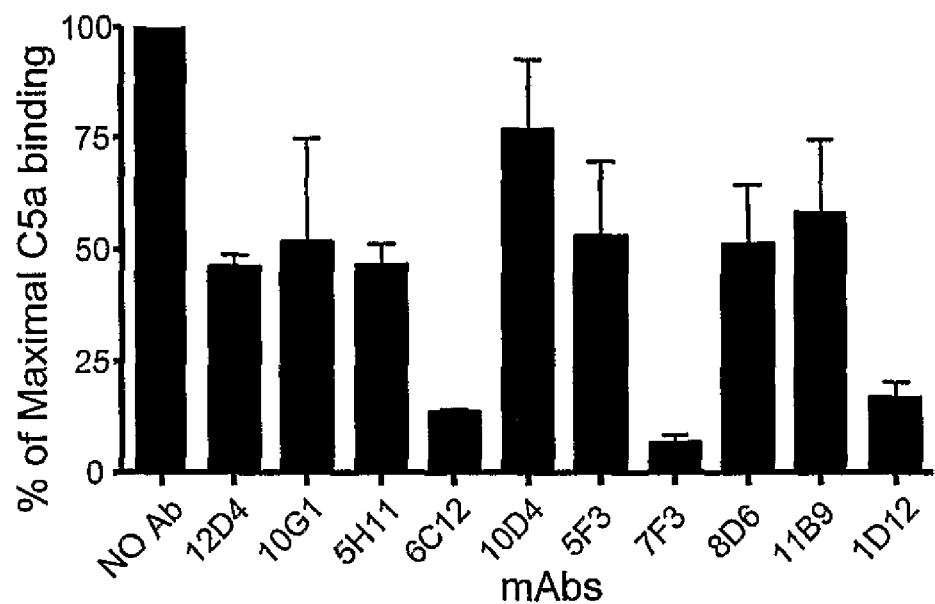
FIG. 1. The anti-human C5aR mAbs generated from mice immunized with L1.2/hC5aR cells inhibited binding of 125I-C5a to human neutrophils to varying degrees. Error bar indicates SD.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, *A Practical Guide to Molecular Cloning*, John Wiley and Sons (1984), J. Sambrook et al., *Molecular Cloning: A Laboratory Manual*, Cold Spring Harbour Laboratory Press (1989), T. A. Brown (editor), *Essential Molecular Biology: A Practical Approach*, Volumes 1 and 2, IRL Press (1991), D. M. Glover and B. D. Hames (editors), *DNA Cloning: A Practical Approach*, Volumes 1-4, IRL Press (1995 and 1996), and F. M. Ausubel et al., (editors), *Current Protocols in Molecular Biology*, Greene Pub. Associates and Wiley-Interscience (1988, including all updates until present), Ed Harlow and David Lane (editors) *Antibodies: A Laboratory Manual*, Cold Spring Harbour Laboratory, (1988), and J. E. Coligan et al., (editors) *Current Protocols in Immunology*, John Wiley & Sons (including all updates until present), and are incorporated herein by reference.

Method of Raising Antibodies

The present inventors have now found that that a knock-in mouse expressing a human polypeptide can be used to develop high affinity antagonistic mAbs against the human polypeptide, through immunization of wild-type mice with cells derived from the knock-in mice.

Accordingly, the present invention provides a method for producing an antibody against a polypeptide of a first species, the method comprising: immunizing a mammal of a second species with cells derived from a transgenic mammal of the second species, wherein the polypeptide of the first species is expressed by the cells derived from the transgenic mammal.

In a preferred embodiment, the polypeptide of the first species is expressed on the surface of the cells derived from the transgenic mammal.

It will be appreciated that the method of the present invention can be used to raise antibodies against a range of different polypeptides. Preferably, the polypeptide is of therapeutic or diagnostic interest. For example, the polypeptide may be a G-protein coupled receptor. In a preferred embodiment, the G-protein coupled receptor is a chemoattractant receptor. Preferably the chemoattractant receptor is C5aR.

The polypeptide is derived from a first species, which may be any species of interest. Preferably, the first species is a species selected for therapeutic or prophylactic treatment. For example, the first species may be a domestic animal, a livestock animal or a human being. In a preferred embodiment, the first species is a human being.

Preferably, the transgenic mammal is a non-human mammal such as a cow, pig, goat, sheep, camel, horse, cat, dog, monkey, baboon, rabbit, guinea pig, rat, hamster and mouse. Rodents such as rats, mice and hamsters are preferred transgenic mammals.

Any cell from the transgenic mammal can be used for the immunization. It is preferred, however, that the cell obtained from the transgenic mammal expresses the polypeptide on its surface at a relatively high density. Expression levels of greater than 100,000 or 200,000 polypeptides per cell are preferred.

It will be appreciated that the preferred cell type will therefore depend on the nature of the polypeptide. For example, if the polypeptide is naturally highly expressed in the liver, the preferred cells derived from the transgenic mammal may be liver cells. Alternatively, if the polypeptide affects immune regulation or inflammatory responses, the preferred cell type may be cells of the immune system, such as antigen presenting cells. Examples of suitable antigen presenting cells include dendritic cells, macrophages, monocytes, neutrophils, eosinophils, basophils, fibroblasts, mast cells, T cells and B cells.

The mammal to be immunized is a mammal of the same species as the transgenic mammal used to obtain cells for immunization. The mammal to be immunized can be any mammal suitable for use in raising antibodies. Again, rodents such as rats, mice and hamsters are preferred mammals to use for immunization.

Techniques for immunization will be well known to those skilled in the art. In one embodiment, for example, the mammal is immunized with cells obtained from the transgenic mammal numerous times at two week intervals.

In a preferred embodiment, the method further comprises preparing hybridoma cells from spleen cells obtained from the immunized mammal after the final immunization. Preferably, the method further comprises screening the hybridoma cells for antibodies that bind to the polypeptide of the first species.

Antibodies produced by this method can then be used to generate recombinant or humanized antibodies, as described in detail below. For example, the CDR regions of the heavy and/or light chains of an antibody produced by the method of the invention may be grafted onto a framework region derived from a different human antibody in order to generate a humanized antibody with similar binding properties to the antibody produced by the method of the invention. Humanized or recombinant antibodies produced in this manner are also encompassed by the present invention.

Polypeptides of a First Species

The present invention relates to a method of raising an antibody against a polypeptide of a first species. In a preferred embodiment, the antibody raised against the polypeptide is suitable for use as a therapeutic or diagnostic agent to treat or diagnose a subject of the first species.

The skilled person will appreciate that the method of the present invention can be used to produce antibodies against a range of biologically active polypeptides. Examples of suitable polypeptides include those which are already targets for production of therapeutic or diagnostic antibodies.

In one preferred embodiment, the polypeptide affects the immune regulation or induction of acute phase inflammatory responses to injury, graft rejection or infection. For example, the polypeptide may be a G-protein coupled receptor. In a preferred embodiment, the G-protein coupled receptor is a chemoattractant receptor. Preferably the chemoattractant receptor is C5aR. Alternatively, the polypeptide may be C5a, CD18, CD147, CD40L, CD25, CD3, TNF-alpha, CD4, IgG1, or CD64 (FcR).

Non-limiting examples of additional polypeptides for use in the present invention include IL-8, gp120, VLA-4, DC11a, VEGF, ICAM-I, CD2, EGFR, E-selectin, Factor VIII, beta2-integrin and EpCAM.

By "a polypeptide of a first species" we mean have a polypeptide which has a sequence homologous to, or preferably identical to, all or a portion of a native sequence derived from a subject of a first species. A polypeptide that has a sequence that is homologous to all or a portion of a native sequence is a biologically active polypeptide that preferably has at least about 80% sequence identity, more preferably at least about 95% amino acid sequence identity, more preferably at least about 96% amino acid sequence identity, more preferably at least about 97% amino acid sequence identity, more preferably at least about 98% amino acid sequence identity, and most preferably at least about 99% amino acid sequence identity with a full length native sequence polypeptide, a native sequence polypeptide lacking a signal peptide, an extra cellular domain of the polypeptide or any other fragment of the full length native sequence.

In the context of the present invention, the polypeptide of the first species is expressed by a transgenic mammal. The transgenic mammal may be produced by introducing a native coding region from a gene of the first species into the genome of the transgenic mammal. It is not necessary, however, to introduce the complete native coding region into the genome of the transgenic mammal. Instead, it may be possible to replace the coding region for at least one domain of the polypeptide (or a substantial part thereof) in the transgenic mammal with the corresponding domain of the polypeptide of the first species. For example, if the polypeptide of a first species is human C5aR, the transgenic mammal may be generated by replacing least one extracellular domain of the endogenous C5aR with the corresponding human C5aR extracellular domain. The human C5aR expressed by the transgenic mammal may thus comprises only one extracellular domain of human C5aR. In another example, the human C5aR expressed by the transgenic mammal comprises intracellular domains of the endogenous C5aR and extracellular domains of human C5aR.

The nucleic acid molecule encoding the polypeptide may be modified in order to enhance expression or stability of polypeptide. For example, nucleic acid properties may be optimized to improve expression yields using one or more of the following strategies: 1) replace imperfect Kozak sequence, 2) reduce 5' GC content and secondary structure of the RNA, 3) optimize codon usage, 4) use an alternate leader sequence, 5) include a chimeric intron, or 6) add an optimized poly-A tail to the C-terminus of the message. Polypeptide properties may also be optimized to improve expression yields using one or more of the following strategies: 1) optimize the signal sequence, 2) optimize the proteolytic processing site, 3) replace one or more cysteine residues in order to minimize formation of improper disulfide bonds, 4) improve the rate or efficiency of protein folding, or 5) increase protein stability, especially proteolytic stability.

Alternatively, modifications may be made to the promoter sequence in order to enhance expression levels of the polypeptide. In one embodiment, the native promoter sequence is replaced with a promoter sequence that expresses the polypeptide in the cell from the transgenic animal that is used to immunize the mammal of a second species.

The polypeptide may also be modified in order to target delivery of the expressed polypeptide to the surface of the transgenic cell. Virtually all cell surface and secreted proteins are expressed as precursors which contain an amino terminal extension, termed the signal peptide, ranging from 5 to 30 amino acid residues in length. The information required for initiation of the secretion process is thought to reside within the short signal peptide extension. The signal peptide is cleaved from the protein upon translocation across the membrane. Additionally, other hydrophobic regions within the protein, termed transmembrane (TM) domains, anchor cell surface proteins to cellular membranes.

The amino acid sequences of many signal peptides are known. Although there is little direct amino acid sequence homology among signal peptides, their overall structure is highly conserved. The intracellular elements responsible for the eukaryotic signal peptide-induced secretion pathway have been well defined and facilitate translocation of the proteins across the endoplasmic reticulum (ER) membrane.

In contrast, certain proteins have a signal sequence that is not cleaved, a "signal anchor sequence," which serves as a transmembrane segment. A signal anchor type I protein has a C-terminus that is located in the cytosol, which is similar to type I membrane proteins, whereas a signal anchor type II protein has an N-terminus that is located in the cytosol.

Thus, surface display of the polypeptide expressed by the transgenic cell may be achieved by producing a fusion protein that contains the polypeptide of interest and a transmembrane domain from another protein that is naturally displayed on the cell surface. Alternatively, a signal peptide that is typically responsible for the secretion of a polypeptide can be modified so that it is no longer contains a site for proteolytic cleavage. This modification to the signal sequence will result in the polypeptide being expressed on the cell surface and not secreted.

Transgenic Animals

Techniques for producing "knock in" transgenic animals are well known in the art. A useful general textbook on this subject is Houdebine, Transgenic animals—Generation and Use (Harwood Academic, 1997)—an extensive review of the techniques used to generate transgenic animals from fish to mice and cows. Of particular interest in the context of the present invention are transgenic non-human mammals such as cows, pigs, goats, horses, etc., and particularly rodents, e.g. rats, mice, hamsters, etc. Preferably, the transgenic animal is a mouse.

Advances in technologies for embryo micromanipulation now permit introduction of heterologous DNA into, for example, fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are transfected with the desired DNA by electroporation, and transgenic animals produced from the infected embryo. In a further preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., *Manipulating the Mouse Embryo*, (Krimpenfort et al., Bio/Technology 9:844 (1991); Palmiter, et al., *Cell*, 41:343 (1985); Kraemer, et al., *Genetic Manipulation of the Mammalian Embryo*, (Cold Spring Harbor Laboratory Press 1985); Hammer, et al., *Nature*, 315:680 (1985); U.S. Pat. Nos. 5,175,385; 5,175,384, the respective contents of which are incorporated herein by reference.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology as described in Schnieke, et al., *Science*, 278:2130 (1997) and Cibelli, et al., *Science*, 280:1256 (1998). Using this method, fibroblasts from donor animals are stably transfected with a plasmid incorporating the coding sequences for a binding domain or binding partner of interest under the control of regulatory. Stable transfectants are then fused to enucleated oocytes, cultured and transferred into female recipients.

Analysis of animals which may contain transgenic sequences would typically be performed by either PCR or Southern blot analysis following standard methods.

By way of a specific example for the construction of transgenic mammals, such as cows, nucleotide constructs comprising a sequence encoding a binding domain fused to GFP are microinjected using, for example, the technique described in U.S. Pat. No. 4,873,191, into oocytes which are obtained from ovaries freshly removed from the mammal. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000 g to visualize the pronuclei for injection and then cultured from the zygote to morula or blastocyst stage in oviductal tissue-conditioned medium. This medium is prepared by using luminal tissues scraped from oviducts and diluted in culture medium. The zygotes must be placed in the culture medium within two hours following microinjection.

Oestrous is then synchronized in the intended recipient mammals, such as cattle, by administering coprostanol. Oestrous is produced within two days and the embryos are transferred to the recipients 5-7 days after estrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example, in WO91/10741.

Transgenic animals comprise an exogenous nucleic acid sequence present as an extrachromosomal element or stably integrated in all or a portion of its cells, especially in germ cells. It is preferred that a transgenic animal comprises stable changes to the germline sequence. A stable change is generally achieved by introduction of the DNA into the genome of the cell. Vectors for stable integration include plasmids, retroviruses and other animal viruses, YACs, and the like. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals. Thus, in a preferred embodiment, the transgenic mammal is homozygous for the knock-in gene.

In a further preferred embodiment, the transgenic non-human mammals of the invention are produced by introducing a human transgene into the germline of the non-human animal. Embryonal stem cell (ES) are the primary type of target cell for introduction of the human transgene into the non-human animal in order to achieve homologous recombination. ES cells may be obtained from pre-implantation embryos cultured in vitro and fused with embryos (Evans, et al., *Nature* 292:154-156 (1981); Bradley, et al., *Nature* 309:

255-258 (1984); Gossler, et al., *Proc. Natl. Acad. Sci U.S.A.* 83:9065-9069 (1986); and Robertson, et al., *Nature* 322:445-448 (1986)). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch (1988) *Science* 240, 1468-1474. The transfected embryonal cells may be incubated in vitro for varying amounts of time, or reimplanted into the surrogate host, or both.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, in transgenic mice, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis. Progeny of the transgenic animals may be obtained by mating the transgenic animal with a suitable partner, or by in vitro fertilization of eggs and/or sperm obtained from the transgenic animal.

Methods of producing transgenic mice via homologous recombination between the endogenous gene and a transgene construct are described by Hanks, et al., *Science* 269:679-682 (1995), which is specifically incorporated herein by reference. It will be appreciated that this can be achieved by, for example, introducing a polynucleotide construct encoding a human polypeptide into the genome of a mammal by targeted integration into the genome of the mammal.

Although not necessary to the operability of the invention, the transgenic animals described herein may comprise alterations to endogenous genes in addition to the genetic alterations described above. Accordingly, the host animals may be both a "knockout" and "knockin" for the gene encoding the polypeptide of interest. Knockouts have a partial or complete loss of function in one or both alleles of an endogenous gene of interest. For example, if the polypeptide of interest is C5aR, the host animal's endogenous C5aR may be "knocked out" and a C5aR derived from a different species "knocked in"). In this example, a polynucleotide construct encoding a full length or fragment of human C5aR may be integrated within the endogenous C5aR sequence, such that following integration, the endogenous C5aR site comprises polynucleotide encoding human C5aR.

With regard to a "knockout", preferably the target gene expression is undetectable or insignificant. For example, a knock-out of a C5aR gene means that function of the endogenous C5aR gene has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. A functional "knock-out" may also be achieved by the introduction of an anti-sense construct that blocks expression of the native genes (for example, see Li, et al. (1996) *Cell* 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

Antibodies

Antibodies produced by the method described above are encompassed by the present invention. Exemplary antibodies include polyclonal, monoclonal, humanized, bispecific and heteroconjugate antibodies.

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(FaV)_2$, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; and (6) Single domain antibody, typically a variable heavy domain devoid of a light chain.

Polyclonal Antibodies

The antibodies produced by the method of the invention may be polyclonal antibodies. Methods of preparing polyclonal antibodies are known to the skilled artisan. Polyclonal antibodies can be raised in a mammal, for example, by one or more injections of the cells expressing the polypeptide of the first species derived from the transgenic mammal and, if desired, an adjuvant. Typically, the cells and/or adjuvant will be injected in the mammal by multiple subcutaneous or intraperitoneal injections. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies

The antibodies produced by the method of the invention may, alternatively, be monoclonal antibodies. Monoclonal antibodies may be prepared using hybridoma methods, such as those described by Kohler, et al. *Nature,* 256:495 (1975). In a hybridoma method, a mouse, hamster, or other appropriate host animal, is typically immunized with the cells expressing the polypeptide of the first species derived from the transgenic mammal to elicit lymphocytes that produce or are capable of producing antibodies that will specifically bind to the polypeptide of the first species.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur, et al., *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against the polypeptide of the first species. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson, et al. *Anal. Biochem.*, 107:220 (1980).

After the desired hybridoma cells are identified, the clones maybe subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Human and Humanized Antibodies

The antibodies of the present invention may be humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al., *Nature*, 321:522-525 (1986); Riechmann, et al., *Nature*, 332:323-329 (1988); and Presta, *Curr. Op. Struct. Biol.*, 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones, et al., *Nature*, 321:522-525 (1986); Riechmann, et al., *Nature*, 332:323-327 (1988); Verhoeyen, et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom, et al., *J. Mol. Biol.*, 227:381 (1991); Marks, et al., *J. Mol. Biol.*, 222:581 (1991)). The techniques of Cole, et al. and Boerner, et, al., are also available for the preparation of human monoclonal antibodies (Cole, et al., *Monoclonal Antibodies and Cancer Therapy*, Alan R. Liss, p. 77 (1985) and Boerner, et al., *J. Immunol.*, 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks, et al., *Bio/Technology* 10:779-783 (1992); Lonberg, et al., *Nature* 368:856-859 (1994); Morrison, *Nature* 368:812-13 (1994); Fishwild, et al., *Nature Biotechnology* 14:845-51 (1996); Neuberger, *Nature Biotechnology* 14:826 (1996); Lonberg, et al., *Intern. Rev. Immunol.* 13:65-93 (1995).

The antibodies may also be affinity matured using known selection and/or mutagenesis methods as are known in the art. Preferred affinity matured antibodies have an affinity which is five times, more preferably 10 times, even more preferably 20 or 30 times greater than the starting antibody (generally murine, humanized or human) from which the matured antibody is prepared.

Bispecific Antibodies

Bispecific antibodies are monoclonal, preferably human or humanized, antibodies that have binding specificities for at least two different antigens. For example, one of the binding specificities may be for C5aR, the other one may be for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein, et al. *Nature*, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker, et al., *Embo. J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh, et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan, et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby, et al. (*J. Exp. Med.* 175:217-225 (1992)) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers (Kostelny, et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger, et al. (*Proc. Natl. Acad. Sci. USA* 90:6444-6448 (1993)) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported (Gruber, et al., *J. Immunol.* 152:5368 (1994)).

Antibodies with more than two valencies are contemplated. For example, trispecific antibodies can be prepared (Tutt, et al., *J. Immunol.* 147:60 (1991)).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO91/00360; WO92/200373; EP03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC) (Caron, et al., *J. Exp Med.*, 176:1191-1195 (1992); Shopes, *J. Immunol.*, 148:2918-2922 (1992)). Homodimeric antibodies with enhanced anti-tumor activity may also be prepared using heterobifunctional cross-linkers as described in Wolff, et al., *Cancer Research*, 53:2560-2565 (1993). Alternatively, an antibody can be engineered that has dual Fc regions and may thereby have enhanced complement lysis and ADCC capabilities (Stevenson, et al., *Anti-Cancer Drug Design* 3:219-230 (1989)).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta, et al., *Science,* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Antibody Isotypes

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared secondarily, from a parental hybridoma secreting monoclonal antibody of different isotype, by using the sib selection technique to isolate class-switch variants (Steplewski, et al., *Proc. Natl. Acad. Sci. U.S.A.,* 82:8653 (1985); Spira, et al., *J. Immunol. Methods,* 74:307 (1984)).

The following Examples provide specific examples of methods of the invention, and are not to be construed as limiting the invention to their content.

EXAMPLES

Experimental Details

Generation of Human C5aR Knock-in Mice

A knock-out/knock-in strategy was adopted to construct a transgenic mouse expressing human C5aR, but not mouse C5aR, under the control of the mouse C5aR gene promoter. The targeting vector comprised a 3.5 kb region of mouse C57BL/6 genomic DNA upstream of the C5aR gene exon 3, human C5aR gene exon 3 coding sequence, mouse C5aR gene 3' untranslated region, phosphoglucokinase promoter and neomycin resistance gene flanked by loxP sites and a 3 kb region of mouse genomic DNA downstream of the C5aR gene in the vector pLOz (Ozgene, Perth, Australia). Genomic DNA fragments were generated using PCR amplification. The vector was transfected into C57BL/6 embryonic stem cells and DNA from G418 resistant colonies was screened by Southern blot. Xba I and EcoR V digested DNA was hybridized with 5' and 3' probe, respectively to identify clones with the correct homologous recombination event at both 5' and 3' ends. Chimeras generated from blastocysts injected with the correctly targeted ES clones were mated with C57BL/6 females. Germline transmission of the human C5aR gene was confirmed by Southern blot of mouse tail genomic DNA. Mice homozygous for the human C5aR gene (hC5Rl$^{+/+}$) were generated and PCR, southern blot, and FACS staining confirmed the absence of mC5aR.

Neutrophil Isolation

Human neutrophils were isolated from the peripheral venous blood of healthy volunteers as previously described (Haslett, et al., *Am. J. Pathol.* 119:101-110 (1985)) with modification. Briefly, blood samples collected into EDTA-coated vacutainers were centrifuged at 400×g for 15 min and then the plasma and buffy coats were removed. Following 1% dextran sedimentation for 30 min, the white blood cells were pelleted by centrifugation at 300×g for 5 min and washed with PBS. The cells were then centrifuged at 500×g for 30 min on a cushion of 65% percoll (density, 1.093 g/ml, Amersham Bioscience). After centrifugation, the neutrophils were re-suspended in PBS. Mouse neutrophils were isolated from both hind leg femurs by forcing 5 ml DMEM (GIBCO) medium with 10% fetal calf serum through the bone with a syringe. Neutrophils were separated by density centrifugation over Ficoll-Paque (Amersham Bioscience). Red blood cells were lysed by hypotonic buffer (155 mM $NH_4Cl$, 10 mM $KHCO_3$, 1 mM EDTA). Cell viability was determined by trypan blue exclusion and the neutrophil pellet was re-suspended in PBS.

Monoclonal Antibody Generation

C57BL/6 mice were immunized with ~2×10$^7$ L1.2 transfectants expressing high levels of hC5aR (Campbell, et al., *J. Cell Biol.* 134:255-266 (1996)), i.p., 5 times at 2 week intervals then once i.v. Four days following the i.v. immunization, the spleen was removed and the cells fused with the SP2/0 cell line using standard procedures. C57BL/6 mice were immunized with ~1×10$^7$ neutrophils isolated from femurs of hC5RJ$^{+/+}$ mice, in a similar fashion: twice i.v., once i.p. and a final i.v. immunization. Hybridomas were grown in DMEM (GIBCO) containing 10% Fetalclone (HyClone) and HAT supplement (SIGMA) and culture supernatant was taken for initial screening. Production of selected antibodies was scaled up and mAb was purified by protein A or G chromatography, concentrated, buffer exchanged, and endotoxins removed. MAb concentration was determined using a mouse IgG ELISA kit (Roche).

Flow Cytometry

To assess reactivity of mAbs against transfected cells or leukocytes, we used indirect immunofluorescence staining and flow cytometry. Cells were washed once with PBS, and re-suspended in 100 µl PBS containing 2% human serum and 0.1% sodium azide (staining buffer), purified antibody, or 50 µl hybridoma culture supernatant. After 20 min at 4° C., cells were washed twice with staining buffer, and re-suspended in 50 µl FITC-conjugated affinity purified F(ab')$_2$ goat anti-mouse IgG (Jackson ImmunoResearch Laboratories) diluted 1:200 in staining buffer. After incubating for 20 min at 4° C., cells were washed twice with staining buffer and analyzed on the FACSCalibur (Becton-Dickinson) to determine the level of surface expression. Propidium iodide staining was used to exclude dead cells.

Binding Assays

Human neutrophils were washed and re-suspended in binding buffer (50 mM HEPES, pH 7.5, 1 mM $CaCl_2$, 5 mM $MgCl_2$, and 0.5% BSA) at 1×10$^7$/ml. For each binding reaction (in a final volume of 120 µl), 40 µl cell suspension (4×10$^5$ cells) with an appropriate amount of anti-hC5aR mAb, isotype matched control mAb or unlabelled human C5a (SIGMA) was incubated at room temperature for 15 min. $^{125}$I-labelled human C5a (Perkin Elmer) was added at a final concentration of 0.4 nM and the reactions were incubated at room temperature for 60 min. Cells were then collected and washed 3 times with binding buffer containing 150 niM NaCl. Cells were then transferred to Opti plates (Perkin Elmer) with MicroScint 20 scintillation fluid and radioactivity counted on TopCount (Packard). Each sample was assayed in triplicate.

Calcium Flux Assay

Freshly isolated human neutrophils were loaded with Fluo-3AM (Molecular Probes) for 30 min at 37° C. as previously described (Ponath, et al., *J. Clin. Invest.* 97:604-612 (1996)). Samples were run on a FACSCalibur flow cytometer and linear fluorescence intensities were measured over time.

Chemotaxis Assays

Human or mouse neutrophils (1-2×10$^5$ cells per well) suspended in chemotaxis buffer (RPMI 1640 with 50% M199 (SIGMA) and 2% Fetal calf serum (HyClone) were placed in the upper chamber of a 12-well transwell plates (Corning Costar Co.) and allowed to migrate for 30 min across a 3 µm filter into the lower chamber containing human or mouse C5a. The number of migrated cells was enumerated on FACSCalibur by counting for 60 seconds. Tight forward angle and side scatter gates were set to exclude debris or irrelevant cells.

Transfection of Expression Vectors into L1.2 Cells

Mouse L1.2 cells were grown in RPMI 1640 (GIBCO) supplemented with 10% Fetal calf serum (HyClone), and transfected using Lipofectamine 2000 (Invitrogen) according to the manufacturer's directions.

K/BxN Rheumatoid Arthritis Model

Serum was collected from K/BxN arthritic mice as previously described (Korganow, et al., *Immunity* 10:451-461 (1999)). Experimental arthritis was induced in recipient mice by injecting 150 µl serum i.p. on days 0 and 2, and disease progress was monitored as described (Lee et al., (2002)). Ankle thickness and clinical scores were determined daily. The clinical score was calculated for each mouse by summing the scores for the four paws: 0—normal, 1—slight redness, 2—red and some swelling, 3—red and major swelling. Anti-hC5aR or isotype control mAbs (1-10 mg/kg in PBS) were injected i.p. on day −1 and 1 (preventative treatment) or day 5 (therapeutic treatment). At day 10, mice were sacrificed and paws were collected for histology. Paws were fixed for 48 hrs in fixing solution (10% phosphate buffered Formalin) and decalcified by treatment with 10% Formic acid in fixing solution for 5 days. Samples were then washed with PBS and embedded in paraffin. Sections of 5 µm thick were stained with H&E.

Statistical Analysis

The statistical significance of differences between independent control and treatment groups in the KxB/N model were determined using the Kruskal-Wallis test, followed bypost hoc analysis with Dunn's Multiple Comparison Test.

Example 1

Generation of mAbs to C5aR Using Transfected L1.2 Cells (Comparative Example)

We raised mAbs to hC5aR, firstly by using a known approach for chemoattractant receptors (Heath, et al., *J. Clin. Invest.* 99:178-184 (1997); Qin, et al., *J. Clin. Invest.* 101: 746-754 (1998); Wu, et al., *J. Exp. Med.* 186:1373-1381 (1997); Qin, et al., *Eur. J. Immunol.* 26:640-647 (1996). Mice were immunized with L1.2 cells (a mouse B cell lymphoma line) expressing very high levels of hC5aR (~80,000 receptors per cell). Five fusions were performed and more than 40 different mAbs identified that reacted specifically with hC5aR transfectants but not with transfectants expressing other closely related chemoattractant receptors, such as CXCR1, CXCR2, or the other C5a binding receptor, C5L2 (Gerard, et al., *J. Biol. Chem.* (2005)). A number of these mAbs inhibited $^{125}$I-labeled human C5a binding to hC5aR transfectants. The lead mAb identified, 7F3, showed potent inhibition of C5a binding (FIG. 1), inhibited chemotaxis of human neutrophils to C5a in a chemotaxis assay and blocked C5a-induced calcium flux in human neutrophils (data not shown).

Example 2

Generation of mAbs to C5aR Using Neutrophils from hC5aR Knock-in Mice

Figure 2:
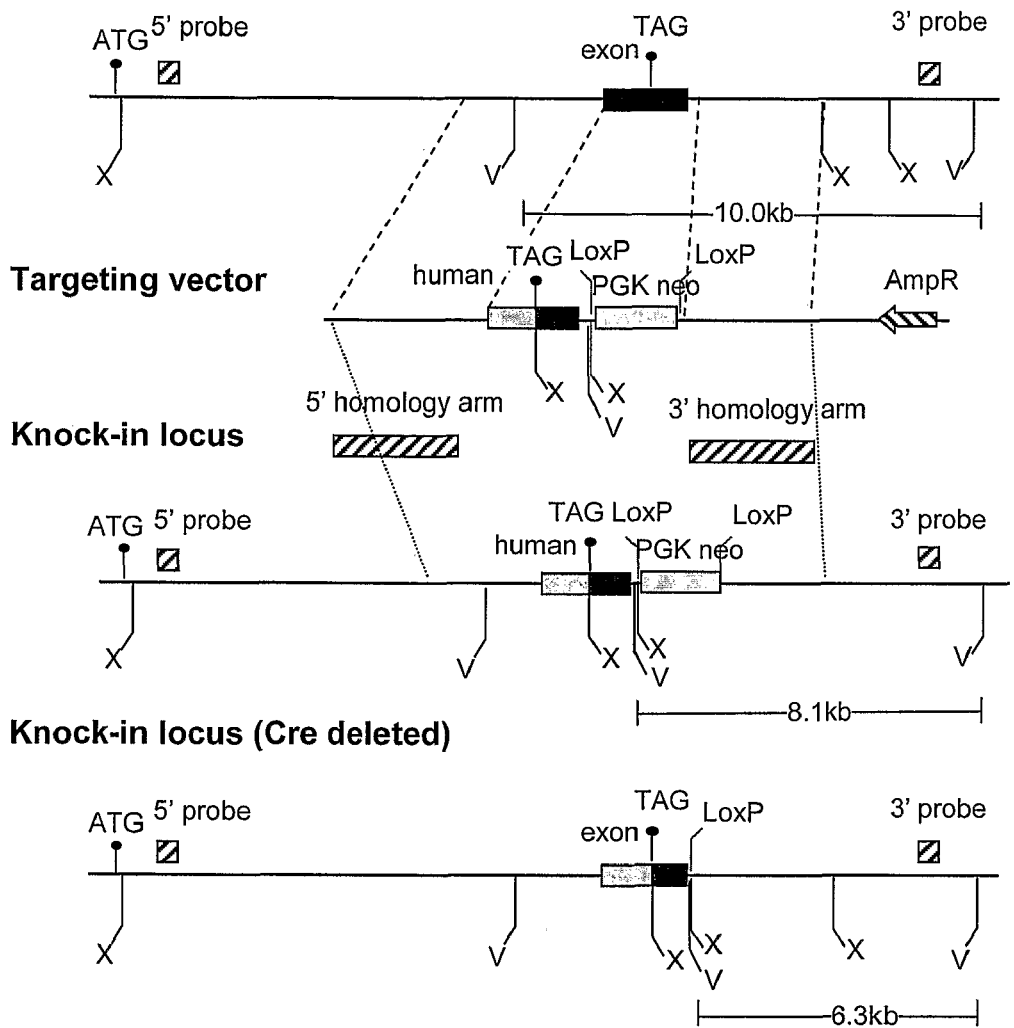
FIG. 2. Map of C5aR locus in wild-type mouse and targeting vector used to construct hC5aR knock-in mice. The mouse C5aR gene exon 3 CDS was precisely replaced with the human C5aR gene exon 3 CDS in the targeting vector. Mouse C5aR gene flanking sequences allowing homologous recombination. The selection marker PGKneo flanked by loxP sites was deleted from the first knock-in mouse using Cre. The 3' and 5' probes were used to confirm the targeting vector had recombined into the mouse C5aR locus correctly. X, XbaI; V, EcoRV.
Figure 3:
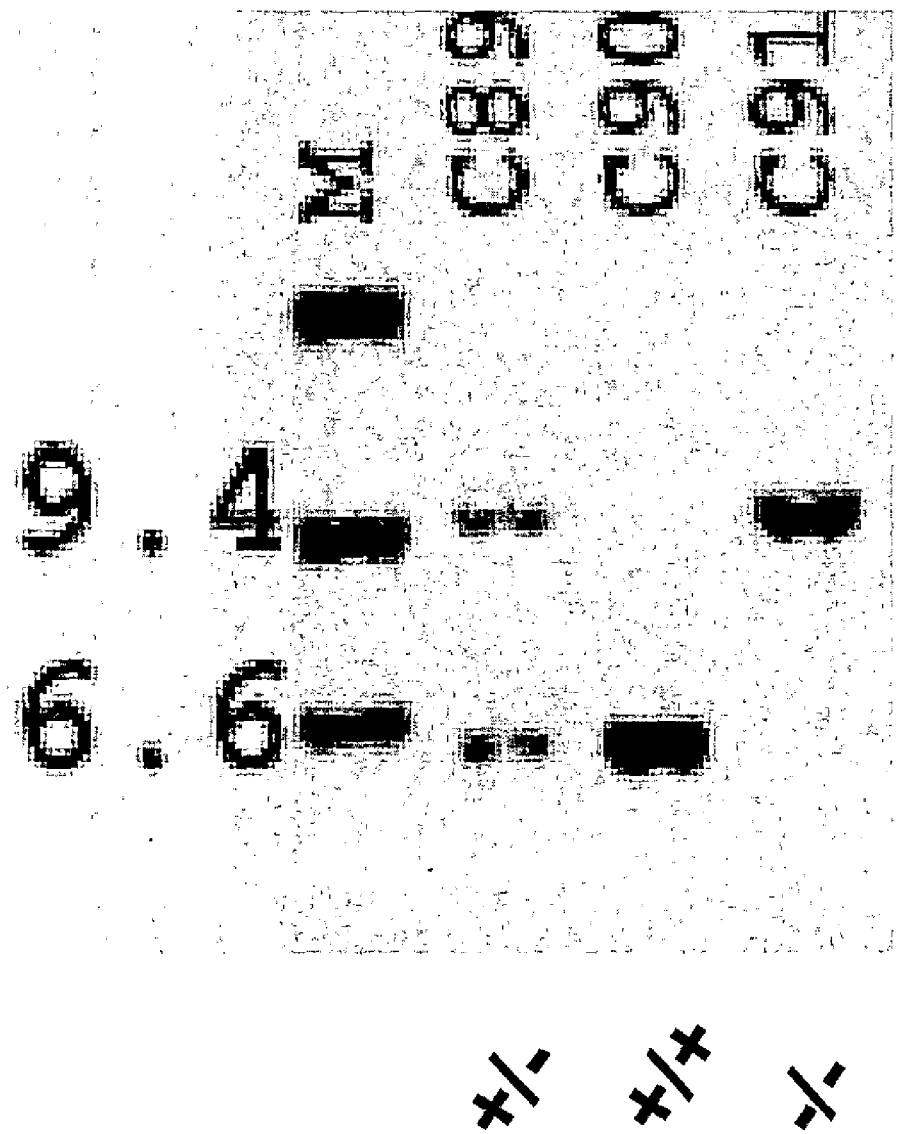
FIG. 3. Southern blot of EcoRV digested genomic DNA from the tails of mice from a cross between heterozygous hC5aR knock-in mice (hC5Rl$^{+/-}$). The blot was hybridized with 3' probe, which distinguishes between the mouse C5aR allele (10.0 kb) and the hC5aR knock-in allele (8.1 kb).
Figure 4:
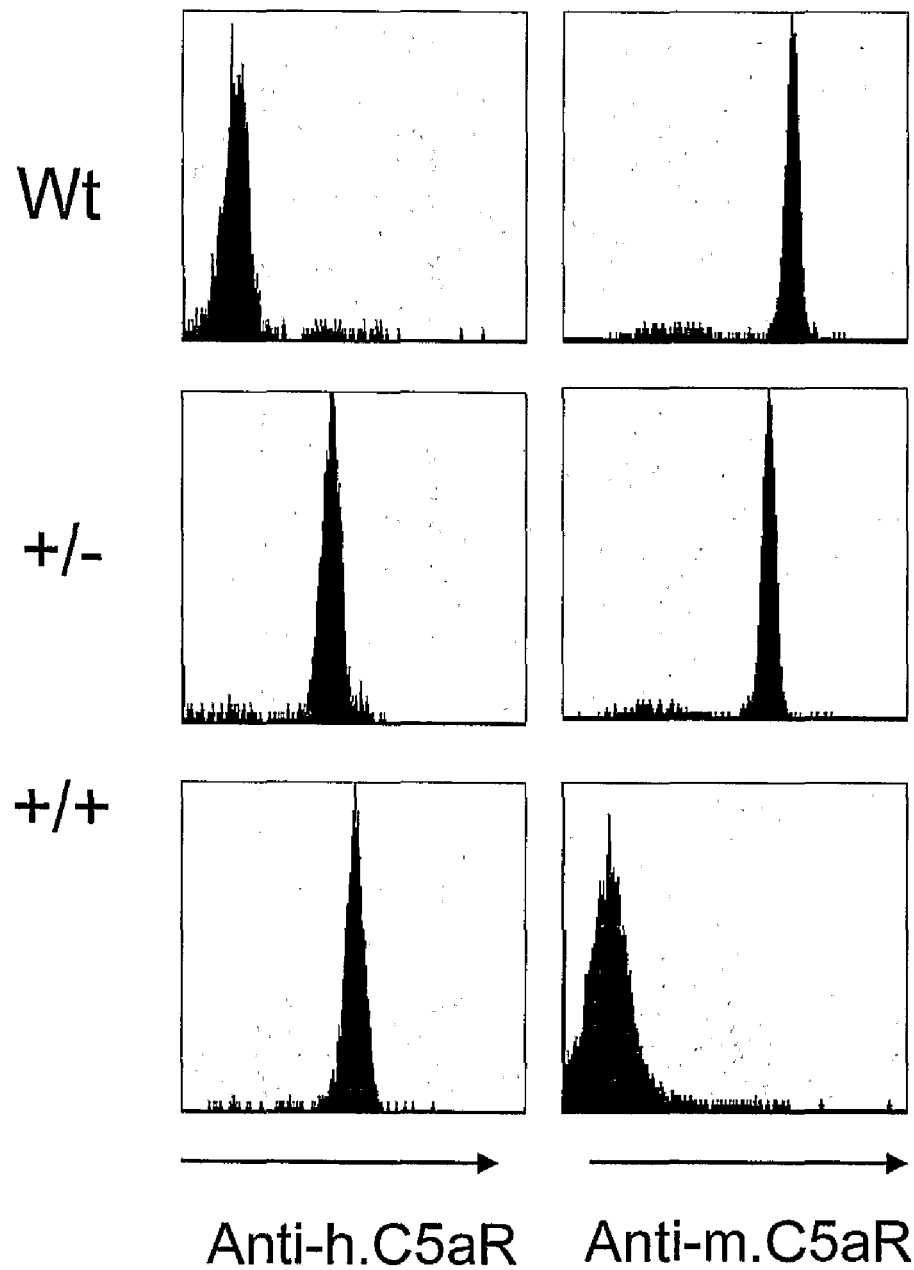
FIG. 4. Expression of C5aR on hC5Rl$^{+/+}$, hC5Rl$^{+/-}$ and wild-type mouse neutrophils. Neutrophils were stained with FITC-conjugated anti-human C5aR mAb (7F3) or anti-mouse C5aR mAb 20/70.

In a second approach to develop potent anti-C5aR mAbs, human C5aR knock-in mice were generated by targeted-homologous recombination at the mouse C5aR gene (C5R1). Simultaneous deletion of the endogenous C5aR coding sequence and its replacement with hC5aR coding sequence was achieved by transfecting mouse embryonic stem cells (ES) cells with targeting construct (FIG. 2). Two ES clones out of 672 screened were identified as containing the correctly targeted hC5aR sequence. Germline transmission of the hC5aR transgene was achieved, and 5 chimeric mice were produced from these ES cells thus establishing the hC5aR knock-in line. The PGK-neo gene flanked by loxP sites was deleted from the knock-in locus using a BL/6 Cre deleter strain. Mice homozygous for the human C5aR transgene ($hC5R1^{+/+}$) were identified by Southern blot (FIG. 3). Neutrophils from these mice were shown to express very high levels of hC5aR, as judged by FACS staining with anti-hC5aR mAbs (FIG. 4). Neutrophils from wild-type mice were unstained by anti-human C5aR mAb 7F3, but were stained intensely by an anti-mouse C5aR mAb, 20/70 (Soruri, et al., (2003)) (FIG. 4). Human and mouse C5aRs share only 65% homology, but importantly for the development of hC5aR knock-in mice, mouse and human C5a binds to human C5aR with similar affinity (Gerard, et al., (1992)) (and our unpublished observations). Neutrophils from $hC5R1^{+/+}$ mice migrated to both human and mouse C5a in a similar fashion.

Figure 5:
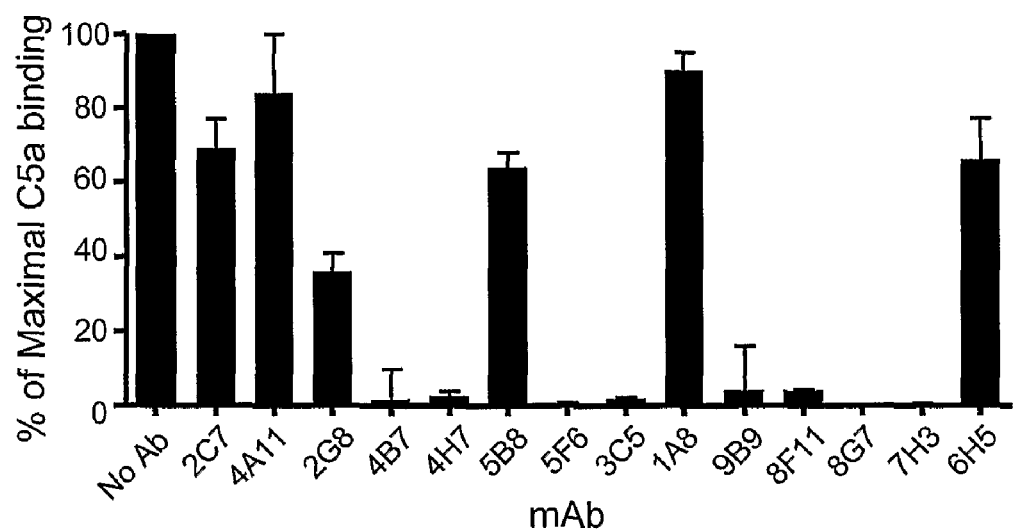
FIG. 5. Antibodies generated from neutrophils of hC5aR$^{+/+}$ mice showed a broad spectrum of $^{125}$I-C5a binding inhibition, ranging from complete inhibition to partial or little inhibition, depending on the mAb clone. Results are representative of at least two independent experiment for each antibody and error bar indicates s.e.m.
Figure 6:
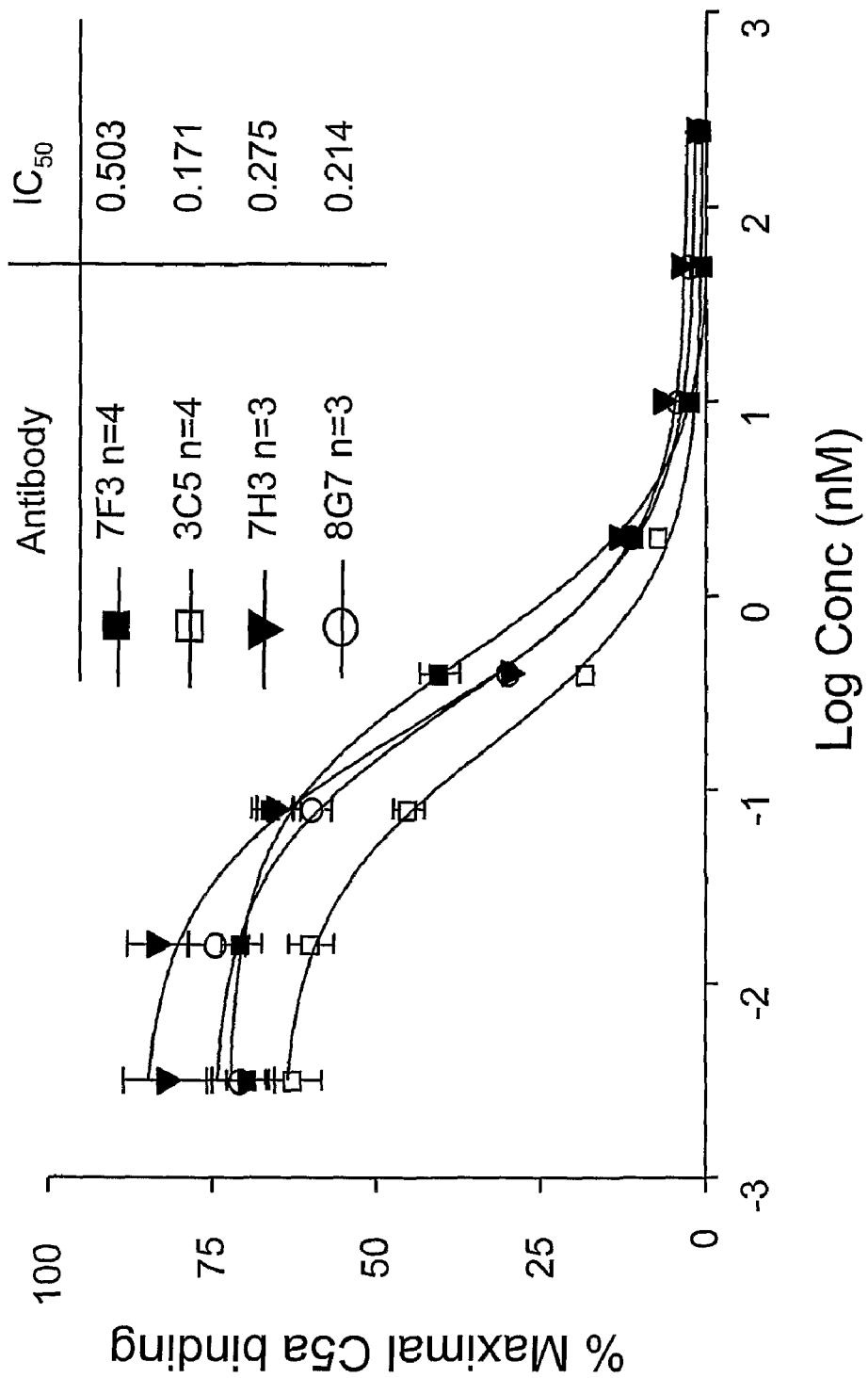
FIG. 6. Anti-C5aR mAbs have sub-nanomolar IC$_{50}$ values. Antibodies generated using hC5Rl$^{+/+}$ mice neutrophils (3C5, 7H3 and 8G7) showed 5-10 fold lower IC$_{50}$ than the best mAb generated using L1.2/hC5aR transfectants (7F3). IC$_{50}$ values were determined from 3 or 4 independent competitive $^{125}$I-C5a ligand binding experiments.
Figure 7:
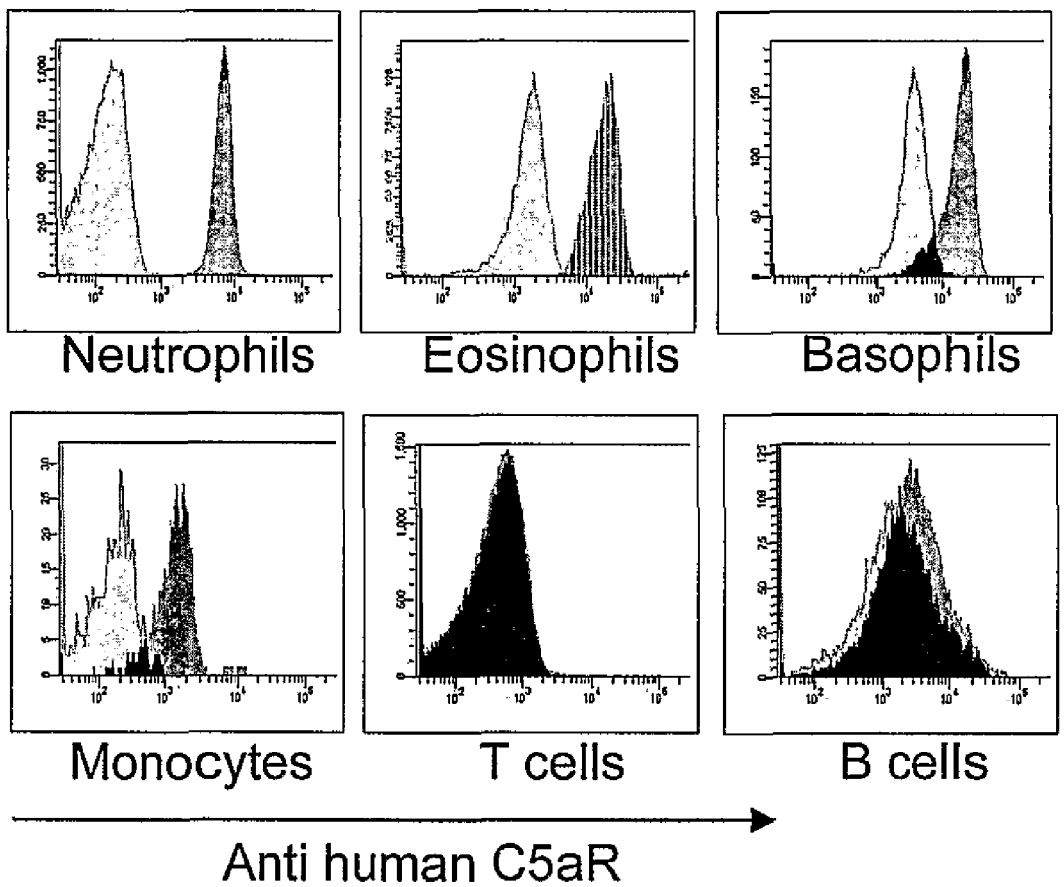
FIG. 7. C5aR expression on human leukocytes. C5aR expression (dark gray) versus control staining (light gray) demonstrated by histogram analysis. Indirect immunofluorescence staining was performed using mAb 7F3 (dark gray), isotype control (light gray) and FITC-conjugated goan anti-mouse IgG.
Figure 8:
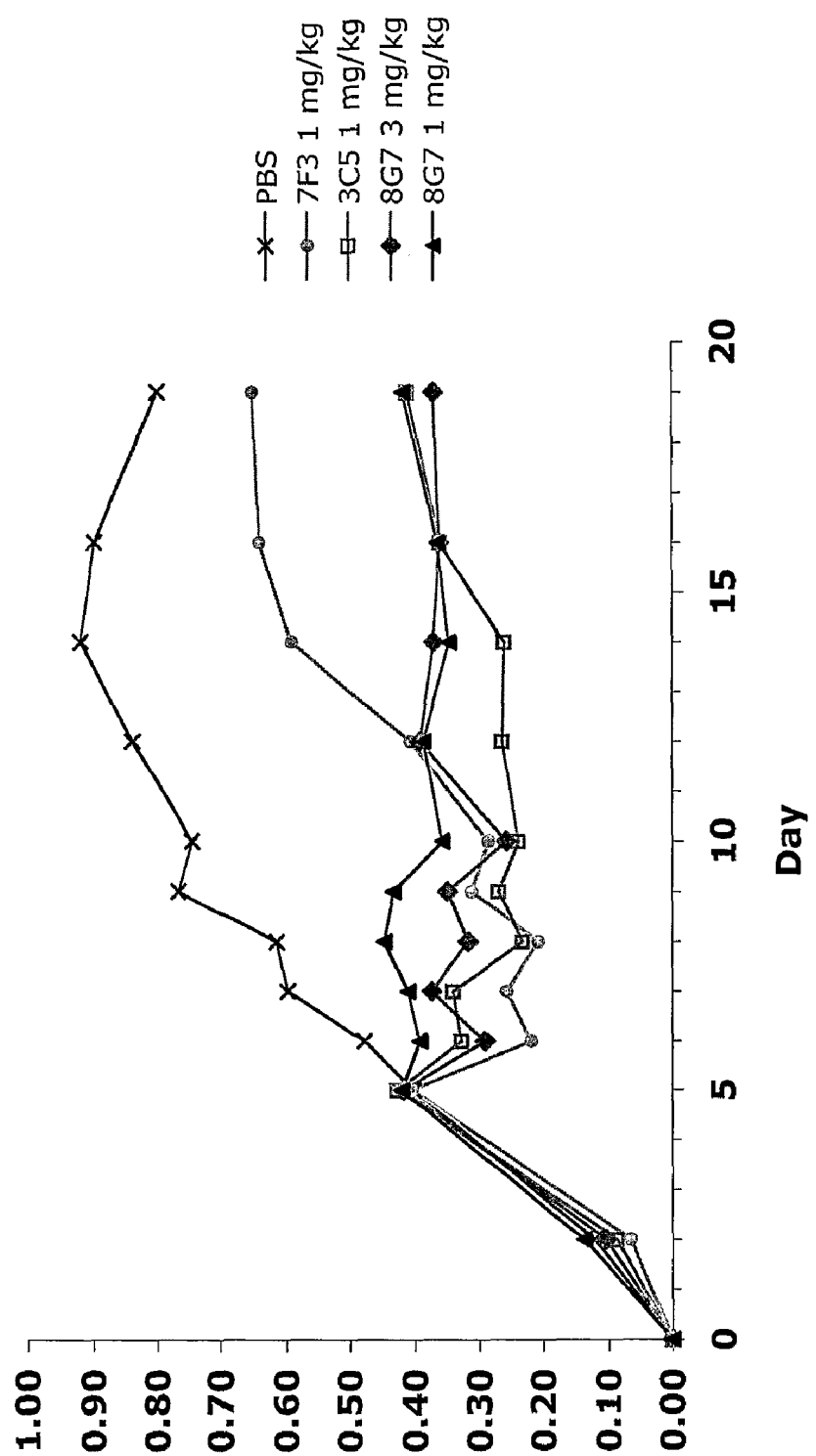
FIG. 8. Comparison of therapeutic efficacy of anti-hC5aR mAbs. hC5Rl$^{+/+}$ mice were injected i.p. with 7F3, 3C5 or 8G7 (at 1 mg/kg or 3 mg/kg in PBS) once, on day 5 after inflammation had developed. Control group received PBS. Graph shows changes in paw (ankle) size from day 0. Group average (n=5-7 per group).
Figure 9:
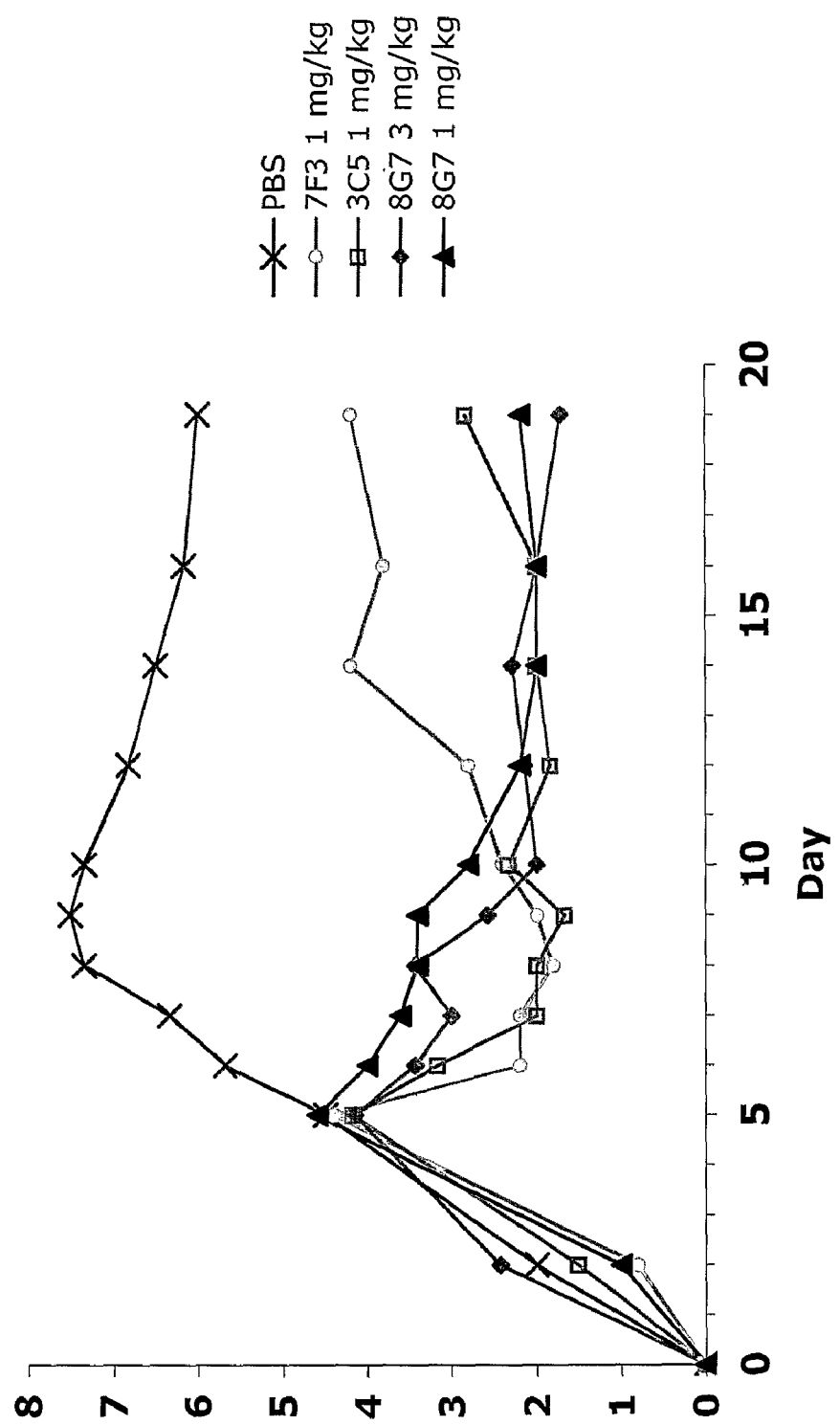
FIG. 9. Comparison of therapeutic efficacy of anti-hC5aR mAbs. hC5Rl$^{+/+}$ mice were injected i.p. with 7F3, 3C5 or 8G7 (at 1 mg/kg or 3 mg/kg in PBS) once, on day 5 after inflammation had developed. Control group received PBS. Graph shows clinical scores. Group average (n=5-7 per group).

From one fusion we generated numerous hC5aR-specific mAbs. Ligand binding assays revealed that many of these mAbs showed superior inhibition of $^{125}$I-labelled C5a binding to human neutrophils than mAb 7F3. Antibodies generated from neutrophils of $hC5aR^{+/+}$ mice showed a broad spectrum of $^{125}$I-C5a binding inhibition, ranging from substantially complete inhibition (e.g. 3C5, 8G7, 7H3) to partial or little inhibition, depending on the mAb clone (FIG. 5). The most potent inhibitor, mAb 3C5, had an $IC_{50}$ of 171 pM, in comparison to an $IC_{50}$ for mAb 7F3 of 503 pM (FIG. 6). The anti-C5aR mAbs generated by immunization of wild-type mice with neutrophils from $hC5R1^{+/+}$ mice were all distinct, in that the amino acid sequences of the heavy chain variable regions were all distinct, indicating they originated from separate clones. The generation of numerous high quality and high affinity anti-C5aR mAbs allowed us to accurately assess C5aR expression on human leukocytes. C5aR was expressed at high levels by neutrophils, eosinophils, basophils, and monocytes, but was absent from all subsets of naïve, memory or effector T cells, as well as most B cells (FIG. 7).

Example 3

Testing of Anti-hC5aR mAbs in a Mouse Rheumatoid Arthritis Model

The development of transgenic mice expressing human molecules is a convenient means to test new human therapeutics, designed for use in humans, in appropriate animal models. C5aR plays an essential role in pathogenesis of inflammatory arthritis in mice. For instance C5aR-deficient mice are protected from arthritis induced by either anti-glucose 6-phosphate isomerase auto-antibodies (Ji, H., et asl., *Immunity* 16:157-168 (2002)) or type II collagen mAbs (Grant, et al., *J. Exp. Med.* 196:1461-1471 (2002)). Anti-hC5aR mAbs were tested for their ability to protect or reverse the progression of experimental arthritis in $hC5R1^{+/+}$ mice. Transfer of serum from arthritic K/BxN mice to healthy mice induces a joint-specific inflammatory reaction that mimics the K/BxN disease (Kouskoff, et al., *Cell* 87:811-822 (1996); Korganow, et al., *Immunity* 10:451-461 (1999)). The $hC5R1^{+/+}$ mice were pre-treated with either anti-hC5aR mAb or isotype matched control mAb on days-1 and 1 and K/BxN serum was injected intraperitoneally (i.p.) on day 0 and 2. After serum transfer, mice treated with control antibody exhibited typical clinical arthritis with joint swelling and inflammatory infiltrates, whereas mice treated with an anti-hC5aR mAb showed a complete absence of inflammation, clinically or histologically. There was no observable difference between $hC5R1^{+/+}$ mice and control littermates in the development of disease (data not shown), indicating that the human C5aR was fully functional, as disease in the KxB/N model is dependent on C5aR (Ji, H., et asl., *Immunity* 16:157-168 (2002); Grant, et al., *J. Exp. Med.* 196:1461-1471 (2002)). More importantly, when antibody was administered 5 days after disease induction, we observed a significant reversal of established inflammation. The effects of mAbs raised against hC5aR-expressing mouse neutrophils (3C5 and 8G7) lasted longer than mAb 7F3. As little as 1 mg/kg of mAb 3C5 was capable of reversing inflammation and providing sustained inhibition.

Discussion

The availability of hC5aR knock-in mice enabled us to generate very high affinity anti-hC5aR mAbs. This presumably relates to the very focused immune response to human C5aR expressed at high density on $hC5R1^{+/+}$ mouse neutrophils. Neutrophils express very high levels of C5aR, up to 200,000 per cell (Gerard, et al., *Ann. Rev. Immunol.* 12:775-808 (1994a)) whereas L1.2 C5aR transfectants express~80,000 receptors, and are 2-3 times larger than neutrophils. Hence the much higher density of C5aR expression achievable on primary mouse neutrophils may be a critical factor. It is also conceivable that antigens expressed on neutrophils evoke better responses because of the antigen presenting function of neutrophils, or their capacity for cell-cell interaction or migration. The development of transgenic mice expressing a well-validated human molecule proved to be a convenient means to test new therapeutics, designed ultimately for use in humans. In our studies, anti-hC5aR mAbs were safe, and surprisingly potent and effective for treating inflammatory arthritis. The relatively low cost of creating knock-in mice, and their potential use in safety and efficacy studies suggests that such mice may become a standard tool for preclinical development. The other important outcome from this study was the development of a mAb that was able to completely reverse the inflammatory process of arthritis. Indeed, we are unaware of any other treatments that so completely prevent or reverse arthritis in these models, to the extent we saw with anti-C5aR mAb treatment. In addition, anti-C5aR mAbs showed this effect at relatively low doses (1 mg/kg), which is considerably less than the doses of anti-C5 antibody used to inhibit arthritis in mice (~40 mg/kg, or 1 mg per mouse) (Ji, H., et asl., *Immunity* 16:157-168 (2002); Wang, et al., *Proc. Natl. Acad. Sci. USA* 92:8955-8959 (1995)). One reason for this may relate to the high concentrations (~180 ug/ml) of C5 that are normally present in blood and tissue fluids. In addition our mAbs recognize C5aR but not the second C5a binding receptor, C5L2, which provides inhibitory signals upon C5a binding (Gerard, et al., *J. Biol.*

Chem. (2005)). Thus a degree of inhibition of the inflammatory response by anti-C5aR mAbs may result from uninterrupted binding of C5a to C5L2. In summary, hC5aR knock-in mice provided a very powerful means to generate high affinity mAbs to human C5aR, and to validate the potency of these antibodies in mouse models of disease, prior to development of a therapeutic for use in humans. The approaches described here for C5aR should be generally applicable to other important therapeutic targets.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for producing an antibody that binds to a human G-protein coupled receptor, the method comprising:
   deriving cells from a transgenic non-human mammal, the cells expressing the human G-protein coupled receptor on their surface; and
   immunizing a mammal with an effective amount of the cells,
   the immunized mammal producing an antibody that binds to the human G-protein coupled receptor.

2. The method according to claim 1, which further comprises preparing hybridoma cells from spleen cells obtained from the immunized mammal.

3. The method according to claim 2, which further comprises screening the hybridoma cells for antibodies that bind to the human G-protein coupled receptor.

4. The method according to claim 1, wherein the antibody is a MAb.

5. The method according to claim 1, wherein the non-human mammal is selected from the group consisting of cow, pig, goat, sheep, camel, horse, cat, dog, monkey, baboon, rabbit, guinea pig, rat, hamster and mouse.

6. The method according to claim 5, wherein the non-human mammal is a mouse.

7. The method according to claim 1, wherein the G-protein coupled receptor is a chemoattractant receptor.

8. The method according to claim 7, wherein the chemoattractant receptor is C5aR.

9. The method according to claim 1, wherein the cells derived from the transgenic mammal are cells of the immune system.

10. The method according to claim 9, wherein the cells derived from the transgenic mammal are antigen presenting cells.

11. The method according to claim 10, wherein the antigen presenting cells are neutrophils.

\* \* \* \* \*